United States Patent [19]

Roos

[11] 4,409,849

[45] Oct. 18, 1983

[54] PROBE FOR COLLECTING TEST PERMEATE FROM A MULTIPLE-MEMBRANE MODULE

[75] Inventor: Martin Roos, Burlington, Mass.

[73] Assignee: Abcor, Inc., Wilmington, Mass.

[21] Appl. No.: 347,559

[22] Filed: Feb. 10, 1982

[51] Int. Cl.³ ............................................. G01N 1/16
[52] U.S. Cl. .................................. 73/863.82; 73/168;
73/864; 210/93
[58] Field of Search ............... 73/863.81, 863.82, 40.5,
73/49.8, 155, 168; 210/85, 92, 93

[56] References Cited

U.S. PATENT DOCUMENTS 2,280,785 4/1942 Boynton ............................... 73/155
2,701,645 2/1955 Eicher ................................. 210/92

FOREIGN PATENT DOCUMENTS 879768 6/1953 Fed. Rep. of Germany ....... 73/40.5

*Primary Examiner*—S. Clement Swisher
*Attorney, Agent, or Firm*—Richard P. Crowley

[57] ABSTRACT

A test probe for collecting test permeate samples from a multiple, reverse-osmosis membrane module, wherein the membrane module has a straight permeate-collection passageway and a plurality of individual, spaced-apart, permeate passageways which permit permeate, from each of a plurality of membranes, to flow into the permeate-collection passageway, and which probe comprises a first outer and a second inner tube concentrically positioned and spaced apart, whereby, on insertion of the test probe into the permeate-collection passageway, the test probe comprises a downstream permeate flow passageway and an upstream permeate flow passageway and a test permeate flow passageway, the test probe having a spacer element at the test end with a radial passageway, and resilient O-rings above and below the spacer element, and a coiled spring to bias the O-rings between an unbiased, nonsealing position and a biased, sealing position, whereby the O-rings extend radially outwardly, to form a seal above and below a test permeate passageway, and permit flow of the permeate from the individual passageways into the test permeate flow passageway, while not disrupting the flow of the upstream and downstream permeate.

12 Claims, 4 Drawing Figures

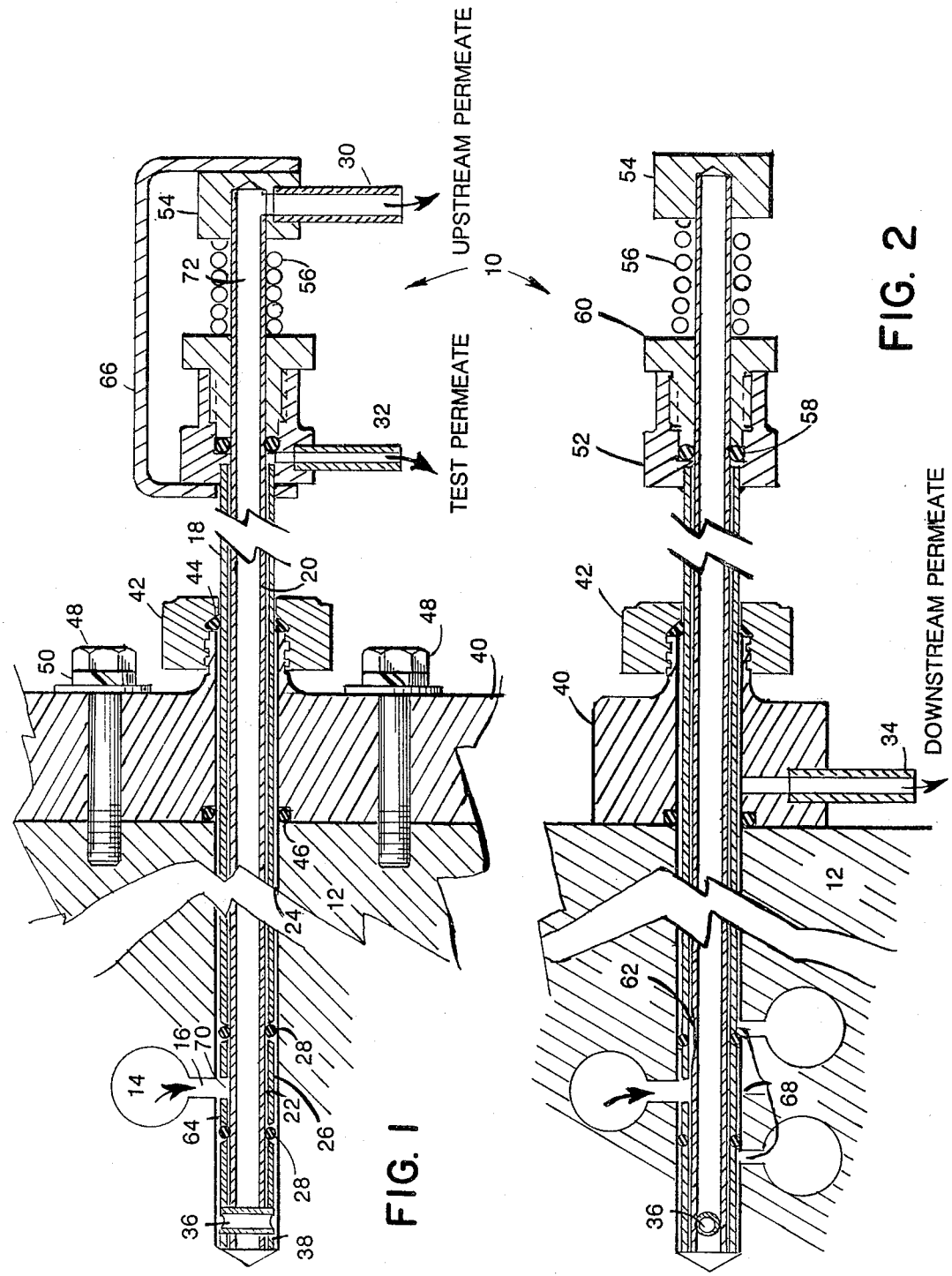

PROBE FOR COLLECTING TEST PERMEATE FROM A MULTIPLE-MEMBRANE MODULE

BACKGROUND OF THE INVENTION

Reverse-osmosis tubular membrane modules typically comprise a plurality of tubular membranes positioned within a tubular outer pressure tube, wherein each end of the outer pressure tube and the inner membrane tube is secured to a pair of tube plate sheets, to form a reverse-osmosis membrane module, such as, for example, of the type shown and disclosed in U.S. Pat. No. 4,309,287, issued Jan. 5, 1982. In such a reverse-osmosis membrane module, each tube sheet is characterized by one or usually more, such as from three to five, straight, tubular, permeate-collection passageways which extend generally perpendicular to the axis of the membrane tube. Individual tubular permeate passageways extend from the end of each of the individual membrane tubes into a permeate-collection passageway, and typically in a staggered, spaced-apart manner, so that permeate flow occurs from the exterior surface of the membrane tube within the outer pressure tube into one or both ends of the tube and into the individual permeate flow passageways. The flow of all of the individual flow passageways is spaced apart and based on either side of the permeate-collection flow passageways and is collected and withdrawn from the membrane module. Often, it is desirable to stack the individual membrane modules, so that the permeate collected in one module flows directly into the permeate-collection flow passageway of the next module, until it is subsequently withdrawn. There are other arrangements by which multiple-tube reverse-osmosis modules, having straight permeate-collection flow passageways, are arranged and employed, and the membrane module, as disclosed in U.S. Pat. No. 4,309,287, issued Jan. 5, 1982, is merely illustrative of reverse-osmosis membrane modules.

During operation of the reverse-osmosis, multiple-tube module, it is desirable; for example, with water-desalination modules, to collect and to test the quality of the permeate produced from individual tubes of a module or a group of modules, in order to determine if the permeate is the desired quality of whether there is a leaking membrane or leaking seal in the module. The quality of the permeate from individual modules can be monitored, by taking a test sample during operation and then subjecting the test sample to suitable analytical means, such as conductivity tests, to determine the amount of low-molecular-weight salt in the test permeate collected. However, where the test permeate from a module indicates an unacceptable permeate from the module, it has been the practice to remove and to replace the entire module; for example, of from a five-to-twenty-tube module, since it is most difficult to test the permeate from individual tubes or a group of tubes within the module, without interrupting the entire operation of the reverse-osmosis process.

Test probes have been disclosed for use in reverse-osmosis or ultrafiltration modules having straight, permeate flow passageways, through the employment of a test probe, to check individual membrane plate elements, such as, for example, set forth in U.S. Pat. No. 4,228,014, issued Oct. 14, 1980. However, present-day test methods are not wholly satisfactory and fail to permit the collecting and testing of individual test permeate from individual membranes, while permitting the high-pressure flow of the downstream and upstream premeate from the test module. Therefore, the present invention is directed to a probe suitable for use in ultrafiltration or reverse-osmosis membrane modules, particularly a multiple-tube or multiple-plate reverse-osmosis membrane module or group of modules, to permit the simple, rapid and easy collecting and testing of permeate from individual tubes or plates, without disruption of the ultrafiltration or reverse-osmosis process and without the disadvantages of prior-art techniques and test probes.

SUMMARY OF THE INVENTION

My invention relates to a probe for collecting a test sample of a permeate from a multiple-tube or multiple-plate membrane module and to the method of use of the probe in collecting the test permeate sample. In particular, my invention concerns a test probe for use in a straight, permeate-collection flow passageway of a high-pressure reverse-osmosis membrane module, which test probe permits the collection of a test sample from an individual membrane tube or plate in the module, by isolation of the tube or plate through the use of the test probe and without disruption of the upstream and downstream permeate flow.

My test probe is suitable for use in those membrane modules or groups of modules, wherein the module or groups of modules have a straight permeate-collection passageway and spaced-apart individual permeate passageways from individual permeate sources leading into the collection passageway, thereby permitting the insertion of the test probe and the sealing off of the individual passageways desired to be tested. My test probe is used by inserting the test probe into the permeate-collection passageway, with a sealing means of the test probe in an unbiased, nonsealing position, so that the test probe may be slid into the straight permeate-collection passageway to the desired distance, typically indicated by graduation marks on the exterior surface of the test probe.

The test probe in position is then placed in a biased position, to seal both above and below the spaced, individual, permeate passageways, by biasing a peripheral sealing means, such as a resilient O-ring above and below the test passageway, outwardly and into a close, sealing contact with the internal wall surface of the straight, permeate-collection passageway. My test probe in the biased position then permits the withdrawal of the test permeate from the individual permeate passageways, while at the same time permitting upstream permeate flow to pass through the interior of the inner tube and permitting downstream permeate to flow from a downstream permeate flow passage about the surface of the outer tube, while the test permeate is withdrawn from the tubular passageways between the first and second inner and outer tubes. The test permeate then may be withdrawn and tested, to determine if the test permeate from the individual permeate passageways, is of satisfactory quality, or whether that individual membrane tube or plate or any seal therein must be replaced. The test probe may be withdrawn by placing the probe in an unbiased position and sliding the probe out of the permeate-collection passageway.

My test probe then comprises a test for collecting test permeate from a membrane module, having a straight permeate-collection passageway therein and a plurality of individual, spaced-apart permeate passageways which direct permeate flow from each individual passageway into the permeate-collection passageway. The test probe may be used for collecting test permeate from a multiple-plate or multiple-tube membrane module, particularly a reverse-osmosis or an ultrafiltration module.

The test probe comprises a first outer tube having a one end and another end, the outer surface of which outer tube forms, on insertion into the permeate-collection passageway, a tubular downstream permeate flow passageway. The test probe also includes a second inner tube generally concentrically positioned within and spaced apart from the first outer tube, to form in the spaced-apart tubular space a tubular test permeate flow passageway, while the inner passageway of the inner tube forms an upstream flow passageway for the withdrawal of an upstream permeate.

The test probe includes a short, tubular, spacer element, the same or similar to the outer tube, at the one test end of the probe, the spacer element having at least one radial passageway therein, which permits permeate flow from a sealed, spaced, individual permeate passageway through the radial passageway and a groove in the inner tube surface and into the tubular test permeate flow passageway formed between the first and second inner and outer tubes.

A resilient, peripheral sealing means, such as a pair of elastomeric O-rings, are placed about each end of the spacer element and spaced along the axial length above and below the test permeate passageway. The resilient sealing means is adapted to move between an untensioned, nonsealing position, wherein the sealing means or O-rings are substantially in alignment with the outer surface of the spacer element, and a tensioned, sealing position, wherein the sealing means extends or bulges radially outwardly and into a sealing position, both above and below the individual permeate passageways, with the inner surface wall in a sealing mode of the permeate-collection passageway. Thus, compression or tension on the peripheral sealing means permits the change between a sealing and a nonsealing position and from a slidable condition to a nonslidable condition of the test probe. Typically, a means is employed, such as a spring-compression bracket, to maintain the resilient sealing means in a compressed state, when the leak test probe is not being employed, in order to avoid any deterioration in the resilient, elastomeric, peripheral sealing means, due to permanent set of the material while in the unbiased or untensioned condition.

The test probe includes an inlet upstream permeate passageway at the one test end of the inner tube and an outlet upstream permeate passageway at the other end, to permit the flow of the upstream permeate during the test operation. The test probe includes an outlet for the test permeate at the other end of the test probe, so that test permeate may be withdrawn from the test permeate passageway for collecting and testing. The test probe includes a downstream permeate outlet, so that the downstream permeate may be withdrawn from the downstream permeate flow passageway, when the test probe is in a test condition.

The test probe includes a seal plate slidably mounted about the exterior of the first outer tube, so that, on insertion of the test probe into the permeate-collection passageway, the outer end of the permeate-collection passageway may be sealed, such as by a seal plate sealed by gaskets against the outer surface of the tube plate and about the exit or inlet of the permeate-collection passageway. The tube plate sealing means and the downstream outlet are positioned between the upper resilient means and the outlet for the test permeate. The tube plate sealing means is slidably mounted, so that the test end of the probe may be inserted in the desired length into the permeate-collection passageway. The test probe, optionally and desirably, includes graduation marks or indicia on the exterior surface of the outer tube, so that, knowing of the position of the individual permeate passageways within the permeate-collection passageway, the test tube may be inserted rapidly to the proper distance prior to sealing the tube plate means against the face of the tube plate.

My test probe allows easy and quick collection and detection of a leaking membrane or seal in a membrane module or a group of modules, so that the individual membrane tube, plate or seal may be detected and replaced, rather than replacing the entire membrane module. My test probe permits a saving in labor time during the initial product quality-control testing of the module prior to shipment, and also during leak detection at a production site, since my test probe permits the flow of downstream and upstream permeate.

In particular, my leak test probe permits a low-cost structural frame design, to house multiple modules, due to the use of a unique tube plate design of the module, since there is no need to remove a module to be leak-tested from the particular stack of modules, and also the replacement of a new membrane tube or plate may be carried out, while the module or group of modules remains in place. The modules, therefore, can be stacked vertically, as well as horizontally, where the tube plates are formed of square or rectangular plates, to make a compact, solid package, with all of the tube plates forming a solid front and rear support structure for the overall membrane apparatus. The rectangular tube plates employed, such as, for example, in U.S. Pat. No. 4,309,287, thus are permitted, due to the test probe, to fill a secondary function of providing structural support in a multiple-module structure.

Thus, my test probe, while permitting the collecting and testing of permeate from individual permeate flow, permits collecting and testing without disruption of the operation of the particular process. The test probe provides for three individual and separate passageways for permeate to flow, when the test probe is inserted into the permeate-collection passageway. The test probe is easily used by inserting the test end of the test probe into the permeate-collection flow passageway, typically by removing a screw plug in the permeate collector at the top of the tube plate means, inserting the test probe and sealing the tube plate means finger-tight against the surface of the tube plate, when the test probe is in the desired position, and then biasing the sealing means, to effect individual sealing, and collecting the test permeate from the test permeate outlet. The test probe is easily removed by placing the resilient sealing means in a nonbiased, slidable condition and untightening the test plate and withdrawing the test probe from the permeate-collection passageway.

My invention will be described for the purpose of illustration only in connection with a particular and preferred test probe employed within a reverse-osmosis, multiple-tube membrane module; however, it is recognized that other persons skilled in the art may make various changes, modifications and improvements in the illustrated test probe and its method of operation, with all such changes,, modifications and improvements falling within the spirit and scope of the invention.

BRIEF DESCRIPTION OF THE DRAWINGS

FIG. 1 is a cross-sectional view of the probe of the invention, with the probe in the nonbiased, insertable condition;

FIG. 2 is a cross-sectional view, at 90 degrees from the view of FIG. 1, of the probe of the invention, with the probe in the biased, sealing condition;

DESCRIPTION OF THE EMBODIMENTS

Figure 3:
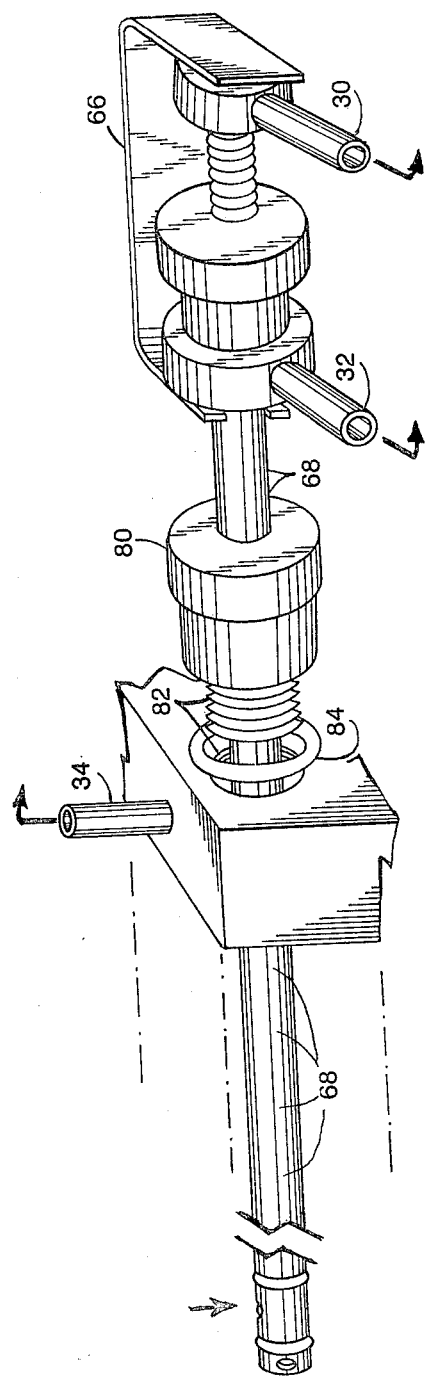
FIG. 3 is a perspective view of a modified test probe of the invention.

With particular reference to FIGS. 1 and 2, there is shown a test probe 10 of the invention shown inserted into a tube sheet 12 of a reverse-osmosis membrane module of the type described in U.S. Pat. No. 4,309,287, which includes a permeate-collection ring cavity 14 and a radial test permeate passageway 16 extending into a central, straight, permeate-collection passageway 64 which extends through the tube sheet of the module, with one end of the collection passageway 64 adapted to receive permeate from an upstream module to which the tube sheet 12 may be sealingly engaged, and to discharge permeate collected from the passageway 64 and upstream passageway at the other end. The test probe includes an elongated outer tube 18, typically of stainless steel, and an elongated inner tube 20, typically of stainless steel, the tubes positioned in a spaced-apart, generally concentric position, so as to define an annular test permeate passageway 22 and an annular downstream permeate passageway 24. The downstream permeate passageway 24 is formed between the outer surface of the outer tube 18 and the inner peripheral wall surface of the permeate-collection passageway 64, while the test permeate passageway 22 is formed by the annular spacing between the inner tube 20 and outer tube 18. The outer tube 18, at the one end or test end of the test probe 10, includes a separate spacer element tube 26 of the same diameter and made of stainless steel as the outer tube, with resilient sealing elements, such as O-rings 28, spaced at either end of the spacer tube 26. The O-rings 28 employed typically are formed of a resilient material, such as an elastomeric material, such as neoprene rubber or of similar material, unaffected by the test permeate and of a material which permits the O-rings to move between a biased and unbiased position, as hereinafter described.

FIG. 1 shows the O-rings in an unbiased or resting position, while FIG. 2 shows the O-rings 28 in a biased or tensioned position. In the embodiment show, the outer tube 18 and the ends of the spacer tube 26, which define a groove for the O-rings 28, are tapered radially outwardly, so as to assist in the outward movement of the O-rings 28 between the biased and unbiased positions. As shown in FIG. 2, in the tensioned, biased position, O-rings 28 are illustrated radially outwardly in a sealing engagement with the internal wall surface of the tube plate 12 of the permeate-collection passageway 64.

The test probe 10 includes a permeate outlet 30, for the withdrawal of the upstream permeate stream, and a test permeate outlet 32, for the withdrawal of test permeate, and a downstream permeate outlet 34, for the withdrawal of downstream permeate. At the one test end of the outer tube 18, there is positioned a lock pin 36 which extends through the outer tube, the outer tube 18 having an open end, the inner passageway of the outer tube defining an upstream inlet permeate passageway, whereby upstream permeate may flow from the one test end about the lock pin 36, which does not fully block the passageway, and may be withdrawn through permeate outlet 30. Lock pin 36 locks in place lock ring 38, which constitutes the one end of the outer tube 18. A seal plate header 40 and an outer seal plate 42 are slidably disposed about the outer tube 18 and contain respective O-ring sealing gaskets 44 and 46, so that the inner surfaces of the header 40 and plate 42 may be placed in a fluid-sealing engagement with the outer wall surface of the tube plate 12 through the use of threadable machine bolts or screws 48 and lock washers 50, thereby providing a seal between the outlet of the permeate-collection passageway 64 in the tube plate 12 and the outer tube 18.

At the other end of the test probe 10, there is welded about the outer surface of the outer tube 18 a spring-retaining block element 52 which contains the test permeate outlet 32, and, at the other end of the outer tube, there is a spring-retaining element 54 which contains the upstream permeate outlet 30 and which is secured to the other end of the inner tube 20. Between spring retainers 52 and 54, there is positioned a coiled spring whose function is to permit the O-rings 28 to move as desired between a biased, tensioned and an unbiased, untensioned position. The O-rings 28 move through axial movement of the inner tube 20 and the lock ring 38, so that O-rings 28 are not squeezed between the ends of the lock ring and the outer tube and the ends of the spacer tube 26. The coiled spring surrounds the outer surface of the inner tube 20 and is disposed at one end within a spring-retaining element 60 which has an O-ring 58, to form a seal with the outer surface of the inner tube 20.

An axially extending, longitudinal groove 62 is provided in inner tube 20 beneath the upstream O-ring, so as to permit test permeate to flow into the test permeate passageway 22 and to flow in the annular cavity therein. In FIG. 2, there is shown a rigid-length, spring-compression bracket 66 which merely permits the spring retainer 54 to be retained in an inward, tensioned position, so that the tensioning of the coiled spring inwardly; that is, between the spring-retaining elements 52 and 54, retains tension on the O-rings 28. The test probe 10 is provided with a plurality of lined or grooved graduation marks 68 on the exterior surface thereof at defined intervals, so that the user may position the test probe 10 to a defined length within the permeate-collection passageway 64. The spacer element 26 also includes an annular hole 70 therein, to permit the introduction of the test permeate into the annular test permeate passageway 22, so that flow may occur from the individual test permeate ring passageway 14 through the radial passageway 16 and passageway 70 and through groove 62 and into the test permeate passageway 22, so that test permeate may be withdrawn through outlet 32.

In operation, the test probe is placed by the user in an unbiased position, so that the O-rings 28 are not under pressure, and the resilient material of the O-rings is substantially equal or less in diameter than the diameter of the outer tube 18 (see FIG. 2). In this condition, the test probe 10 may be slid by the user into the permeate-collection passageway to a defined length, based on the graduation marks 68, so that the annular hole 70 rests about or adjacent the desired radial passageway 16, so that test permeate may be withdrawn through ring cavity 14. The test probe 10 is then placed in a biased condition manually or by the use of the spring-compression bracket 66. When the test probe 10 is placed in the biased, tensioned position, the outward movement of the O-rings 28, caused by the pressure exerted by the one end of the outer tube 18 and each end of the spacer tube 26 and the one end of the lock ring 38, forces the resilient O-rings 28 radially outwardly; for example, 1/32nd to ⅛th of an inch, and into sealing engagement with the internal wall surface of the collection passageway 64; thus, effectively sealing the test radial passageway 16, while the outer "O" ring 28, adjacent to lock ring 38, also seals the permeate passageway 22. Therefore, the taper must be such as not to cause "O" ring detachment from surface of tube 20, the maximum "O" ring size is selected to allow minimum clearance during sliding. Of course, the spacer tube 26 may be of any defined length, but typically has a length sufficient to bridge the diameter of the radial passageway 16, so as to seal off effectively the passageway.

With the test probe now in position within the tube sheet in the defined area, the seal plate header 40 and outer seal plate 42 are secured in position through machine bolts 48 and lock washers 50, to effect a seal about the exit of the permeate-collection passageway 64. Once the seal is effected, then test permeate may be withdrawn from the particular radial passageway 16, while all radial passageways, which extend into the permeate-collection passageway 64 downstream, may be permitted to flow and discharge through downstream permeate annular passageway 24 and withdrawn through outlet 34, while upstream permeate of all radial cavities upstream of the test cavity 14 is permitted to flow into the outer end of the outer tube 18 about lock pin 36 and into the upstream permeate passageway 72 and withdrawn through upstream permeate outlet 30.

FIG. 3 is an illustrative view of a modified test probe, which illustrates more particularly the graduation marks 68 on the outer tube, but in which the seal plate header 40 and outer seal plate 42 of the test probe of FIGS. 1 and 2 have been replaced by a single, threadable, plastic cap 80 having extending threads 82 and an internal O-ring 84. The cap 80 in use is threaded by manual operation into a threaded mating end of the permeate-collection passageway in the tube plate 12, rather than employing the seal plate and headers and machine bolts and lock washers, as in FIGS. 1 and 2. The seal is effected through the use of the O-ring gasket 46 at the exit of the permeate-collection passageway, so that permeate flow is prevented between the collection passageway and the cap, while an internal O-ring 84 provides for a sealing engagement about the outer tube of the test probe. The cap 80 is slidably mounted on the outer ring, so that the outer tube may extend the desired depth into the permeate-collection passageway. However, on tightening of the cap 80, the seal is effected about the permeate-collection passageway and about the outer tube of the test probe.

Figure 4:
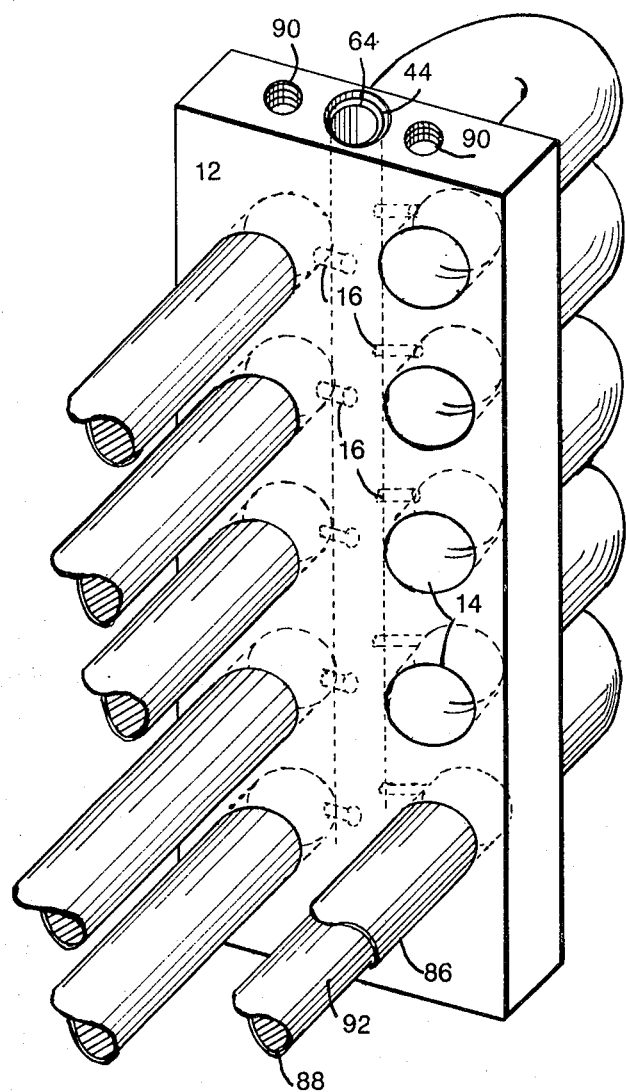
FIG. 4 is a perspective, partially cross-sectional view of a tube plate of a multiple-tube membrane module.

FIG. 4 is an illustration of a rectangular tube plate sheet, as in U.S. Pat. No. 4,309,287, showing a single permeate-collection passageway 64, although typically such tube plates may contain a plurality of collection passageways, and showing a plurality of spaced-apart permeate cavities 14 and radial cavities 16 leading to the permeate-collection passageway 64, with the lower part of the tube plate 12, for illustrative purposes, showing a number of membrane tubes in place comprising an outer pressure tube 86, an inner supported membrane tube 88 spaced apart, to define an annular permeate cavity 92, whereby permeate would flow in the cavity to ring cavity 14 and radial passageway 16 and into passageway 64. This illustration of a tube plate, in a typical tubular reverse-osmosis membrane module, illustrates that the test probe may be inserted into the passageway 64 at any desired length, to determine and to test the permeate from any particular individual tube or groups of tubes, where the spacer tube is spaced apart to cover more than one test permeate inlet.

My test probe is particularly adapted to collect permeate for testing in membrane modules and to overcome many of the disadvantages of the prior art probes and methods of collecting test permeate.

What I claim is:

1. A probe for collecting test permeate from a membrane module having a straight permeate-collection passageway therein and a plurality of individual, spaced-apart permeate passageways, which permits permeate, from test membrane passageways, to flow into the permeate-collection passageway, which test probe comprises:

(a) a first, outer, elongated tube having a one end and another end and which includes, at the one end, a tubular lock ring and an adjacent tubular spacer element having a radial passageway therein, and which tube, on insertion of the one end into the permeate-collection passageway, forms a downstream permeate flow passageway between the outer surface of the tube and the inner surface of the permeate-collection passageway;

(b) a second, inner, elongated tube having a one end and another end and generally concentrically positioned within and spaced apart from the first outer tube, to form in the spaced-apart tubular passageway between the first and second tubes a test permeate flow passageway for the removal of test permeate, and to form in the inner passageway of the second inner tube an upstream permeate flow passageway for the withdrawal of upstream permeate from the permeate-collection flow passageway, the lock ring secured at the one end of the inner tube for axial movement therewith;

(c) resilient, peripheral sealing means about the one and the other ends of the spacer element, the resilient sealing means adapted, with the axial movement of the inner tube, to move between an untensioned position, wherein the outer tube may be inserted slidably into the permeate-collection passageway, and a tensioned position, wherein the sealing means extends radially outwardly and into a sealing position, with the inner surface walls of the permeate-collection passageway above and below the individual permeate passageways, from which test permeate is to be withdrawn;

(d) an inlet at the one end and an outlet at the other end of the second inner tube, to permit the withdrawal of upstream permeate from the upstream permeate passageway;

(e) an outlet at the other end of the first outer tube to permit the withdrawal of downstream permeate from the downstream passageway;

(f) means to bias the sealing means between the sealing and the nonsealing position, by tensioned axial movement of the second inner tube and the lock ring; and (g) sealing means slidably mounted on the first outer tube and adapted to seal the inlet of the permeate-collection flow passageway, after the outer tube has been inserted to its desired length into the permeate-collection flow passageway, whereby, on insertion of the probe into a straight permeate-collection passageway to a desired length, test permeate from an individual permeate passageway is permitted to flow from the individual passageway to the test permeate passageway for collecting and testing, while upstream and downstream permeate is permitted to flow through the upstream permeate and downstream permeate flow passageways, when the bias means are in the tensioned position and the peripheral sealing means are in a sealed position in the permeate-collection passageway.

2. The probe of claim 1 wherein the resilient peripheral sealing means comprises elastomeric O-rings at the one and the other ends of the spacer elements.

3. The probe of claim 1 wherein one end of the first outer tube and one end of the lock ring and both ends of the spacer elements adjacent the resilient peripheral sealing means are tapered radially outwardly, whereby the resilient peripheral sealing means in a biased position are forced radially outwardly.

4. The probe of claim 1 which includes a rigid bracket means to maintain the probe in a tensioned biased condition, when the probe is not in use, in order to avoid permanent set of the resilient peripheral sealing means.

5. The probe of claim 1 wherein the bias means comprises a coiled spring about the other end of the first outer tube and positioned between the secured upstream permeate outlet and the test permeate outlet.

6. The probe of claim 1 which includes an outer longitudinal groove in the surface of the second inner tube extending beneath the upstream resilient sealing means.

7. The probe of claim 1 wherein the slidable sealing means includes a threadable sealed cap slidably mounted about the other end of the first outer tube, the cap including the downstream permeate outlet and adapted to be sealed threadably into a mating outlet of the permeate-collection passageway.

8. A probe for collecting test permeate from a membrane module having a straight permeate-collection passageway therein and a plurality of individual, spaced-apart permeate passageways, which permits permeate, from test membrane passageways, to flow into the permeate-collection passageway, which test probe comprises:

(a) a first, outer, elongated tube having a one end and another end and which includes, at the one end, a tubular lock ring and an adjacent tubular spacer element having a radial passageway therein, and which tube, on insertion of the one end into the permeate-collection passageway, forms a downstream permeate flow passageway between the outer surface of the tube and the inner surface of the permeate-collection passageway;

(b) a second, inner, elongated tube having a one end and another end and generally concentrically positioned within and spaced apart from the first outer tube, to form in the spaced-apart tubular passageway between the first and second tubes a test permeate flow passageway for the removal of test permeate, and to form in the inner passageway of the second inner tube an upstream permeate flow passageway for the withdrawal of upstream permeate from the permeate-collection flow passageway, the lock ring secured at the one end of the inner tube for axial movement therewith;

(c) resilient, peripheral sealing means comprising O-rings and placed about the one and the other ends of the spacer element, the resilient sealing means adapted, with the axial movement of the inner tube, to move between an untensioned position, wherein the outer tube may be inserted slidably into the permeate-collection passageway, and a tensioned position, wherein the sealing means extends radially outwardly and into a sealing position, with the inner surface walls of the permeate-collection passageway above and below the individual permeate passageways, from which test permeate is to be withdrawn;

(d) one end of the first outer tube and one end of the lock ring and both ends of the spacer elements adjacent the resilient peripheral sealing means tapered radially outwardly, whereby the resilient peripheral sealing means in a biased position are forced radially outwardly;

(e) an outer longitudinal groove in the surface of the second inner tube extending beneath the upstream resilient sealing means;

(f) an inlet at the one end and an outlet at the other end of the second inner tube, to permit the withdrawal of upstream permeate from the upstream permeate passageway;

(g) an outlet at the other end of the first outer tube to permit the withdrawal of downstream permeate from the downstream passageway;

(h) means to bias the sealing means between the sealing and the nonsealing position, by tensioned axial movement of the second inner tube and the lock ring, the bias means comprising a coiled spring about the other end of the first outer tube and positioned between the secured upstream permeate outlet and the test permeate outlet; and (i) sealing means slidably mounted on the first outer tube and adapted to seal the inlet of the permeate-collection flow passageway, after the outer tube has been inserted to its desired length into the permeate-collection flow passageway, whereby, on insertion of the probe into a straight permeate-collection passageway to a desired length, test permeate from an individual permeate passageway is permitted to flow from the individual passageway to the test permeate passageway for collecting and testing, while upstream and downstream permeate is permitted to flow through the upstream permeate and downstream permeate flow passageways, when the bias means are in the tensioned position and the peripheral sealing means are in a sealed position in the permeate-collection passageway.

9. A method of collecting test permeate from a multiple-membrane module having a straight permeate-collection passageway and a plurality of spaced-apart, individual permeate passageways which discharge permeate into the permeate-collection passageway, which method comprises:

(a) inserting an elongated test probe, comprising spaced-apart, concentric, inner and outer tubes, into the permeate-collection passageway a defined distance, the test probe at the one end having a pair of spaced-apart, peripheral, resilient O-rings and a radial passageway in the outer tube, the test probe in position defining a downstream permeate passageway, an upstream permeate passageway and a test permeate passageway;

(b) forcing the O-rings peripherally and radially outwardly, to extend beyond the diameter of the outer tube and into a fluid-sealing relationship with the interior wall surface of the permeate-collection passageway just above and below the individual permeate passageways where permeate is to be collected; and (c) withdrawing test permeate from the sealed, individual permeate passageways by withdrawal of the test permeate through the radial passageway between the O-rings and from the test probe, while withdrawing upstream and downstream permeate from the upstream and downstream permeate passageways of the test probe.

10. The method of claim 9 which includes:

(a) removing the force on the O-rings and permitting the O-rings to return to an unbiased position; and (b) withdrawing the test probe from the permeate-collection passageway.

11. The method of claim 9 which comprises forcing the O-rings outwardly by the axial movement of the inner tube with respect to the outer tube.

12. The method of claim 9 wherein the membrane module comprises a reverse-osmosis, multiple-tube membrane module.

* * * * *